United States Patent [19]

Atkinson et al.

[11] Patent Number: 5,443,461

[45] Date of Patent: Aug. 22, 1995

[54] SEGMENTED DEVICE FOR SIMULTANEOUS DELIVERY OF MULTIPLE BENEFICIAL AGENTS

[75] Inventors: Linda E. Atkinson, Portola Valley; John T. Dunn, Palo Alto; Robert M. Gale, Los Altos; David L. Rivera, San Jose, all of Calif.

[73] Assignee: ALZA Corporation, Palo Alto, Calif.

[21] Appl. No.: 114,800

[22] Filed: Aug. 31, 1993

[51] Int. Cl.$^6$ .............................................. A61K 9/22
[52] U.S. Cl. .................................. 604/892.1; 424/473
[58] Field of Search ................. 604/265, 890.1, 891.1, 604/892.1; 424/473

[56] References Cited

U.S. PATENT DOCUMENTS

| | | |
|---|---|---|
| 3,967,618 | 7/1976 | Zaffaroni . |
| 4,237,885 | 12/1980 | Wong et al. . |
| 4,455,143 | 6/1984 | Theeuwes et al. .............. 604/892.1 |
| 4,596,576 | 6/1986 | de Nijs ............................... 604/892 |
| 4,673,565 | 6/1987 | Di Luccio et al. ............... 424/443 |
| 4,720,384 | 1/1988 | Di Luccio et al. ............. 604/892.1 |
| 4,851,216 | 7/1989 | Lee . |
| 4,957,119 | 9/1990 | de Nijs . |
| 5,150,718 | 9/1992 | de Nijs ............................... 128/832 |

Primary Examiner—Randall L. Green
Assistant Examiner—P. Zuttarelli
Attorney, Agent, or Firm—Richard T. Ito; Steven F. Stone; Edward L. Mandell

[57] ABSTRACT

Diffusional delivery devices are constructed in two or more compartments, each containing a separate drug or other beneficial agent, and each arranged to permit diffusion of the agent out of the device through an individually-characterized agent-permeable wall segment. The diffusion rates of the various agents relative to one another are set and controlled by the parameters of the individual wall segments, such as the surface area of the wall segment, the average thickness of the wall segment, and the permeability of the wall segment for the particular agent. The permeability may be varied by variations in the chemical composition of the wall segment. Using these parameters rather than blending the agents at calculated ratios in a single formulation for diffusion through a single wall permits a wider range of, and greater flexibility in, variation between the diffusion rates of the different agents. This is of value when the simultaneous administration of agents at a specified ratio is desired.

18 Claims, 1 Drawing Sheet

SEGMENTED DEVICE FOR SIMULTANEOUS DELIVERY OF MULTIPLE BENEFICIAL AGENTS

FIELD OF THE INVENTION

This invention lies in the field of controlled— or sustained-release systems for the delivery of drugs, nutrients and the like, which may be referred to generally as "beneficial agents." In particular, this invention offers an improvement in the technology of diffusional delivery systems, which are generally in the form of capsules designed to slowly release a beneficial agent through the capsule wall by diffusion. More particularly, the invention relates to the simultaneous release of two or more beneficial agents from a single delivery device.

BACKGROUND OF THE INVENTION

Various types of delivery capsules have been developed for the controlled and sustained release of beneficial agents by diffusion through the capsule wall. The rate of release of the beneficial agent is controlled by combining the agent with an inert core material to a specified dilution and/or by formulating and manufacturing the membrane used to form the capsule wall in a manner which will result in the desired permeability. Polymeric membranes can be varied by such means as varying the degree of crosslinking or by using block copolymers and varying the relative amounts of the different blocks. Further control of the release rate can be obtained by varying the membrane thickness and total exposed surface area (i.e., the size of the capsule).

Certain therapies or regimens require, or would benefit from, the administration of more than one beneficial agent at the same time. This is true for the administration of a variety of drugs, medicaments and nutriments, in a range of environments extending from veterinary medicine to human drug administration as well as nonphysiological environments. In some cases, particularly physiological environments, the two or more beneficial agents are most effective when they are administered at specified rates relative to each another. Whether the ratio of these specified rates is 1.0 (on a mole or weight basis) or something other than 1.0, deviations from the specified ratio can result in a loss of effectiveness, the inducement of undesirable side effects, or in some cases toxicity.

The placement of a blend of the beneficial agents in a single capsule in a proportion equal to the desired delivery rate ratio will not always achieve the desired result. In many cases, the agents will not diffuse together through the capsule membrane at the same ratio as they exist in the blend. The ratio would instead be dependent on the inherent ratio of the normalized permeation rates for the beneficial agents through the membrane. Flexibility would therefore be limited to the selection of suitable polymer candidates for the membrane, and the range of, and degree of control over, the delivery rate ratio which one might obtain in so doing is extremely limited.

For beneficial agents which are solid, a delivery rate approaching zero-order for any single agent over the life of the capsule is achieved by combining the agent with a liquid, semi-solid or solid solvent in the capsule, with the amount of agent present exceeding the solubility limit of the agent in the solvent. Release of the agent from the capsule in such a system involves diffusion of the dissolved agent through the solvent, across the solvent/membrane interface and through the membrane for release, while undissolved agent simultaneously dissolves into the solvent to replace the released agent, thereby maintaining a substantially constant level of agent dissolved in the solvent (i.e., the saturation concentration). For blended agents, the dominant factors in determining the delivery rate ratios will be the rates of dissolution of the agents in the solvent, the rates of diffusion of the agent through the solvent, and the rates of diffusion of the agents through the membrane. These factors are variable only by the choice of solvent and membrane, and when a common solvent and a common membrane material are used, the range of delivery rates which one can obtain is limited even further.

Alternatively, the need for maintaining a specified delivery rate ratio can be met by using a separate capsule for each beneficial agent. This is clearly undesirable, however, for those capsules designed for implantation subcutaneously or in a vesicle or organ of a living animal or human, since the presence of two or more capsules will compound the disruption which even a single capsule might create in the normal physiological activity of that vesicle or organ. In addition, if one capsule malfunctions, the desired delivery ratio will be lost. Further, complete therapy in a single implantable capsule is more acceptable to patients and more efficient to insert and remove, with both humans and animals.

SUMMARY OF THE INVENTION

The present invention resides in a unique means of delivering two or more beneficial agents simultaneously to an environment of use through the walls of a single delivery device at a specified ratio of delivery rates. The ratio of delivery rates from the device remains constant for the duration of use. According to this invention, the delivery device is divided into compartments, one for each beneficial agent, with the walls of the various compartments differing from each other in one or more of the following parameters:

(i) surface area,
(ii) average wall thickness, and
(iii) permeability.

Control of the delivery rates is thus transferred to these three parameters, which provide a full range of flexibility and variation, rather than relying on the quantities, concentrations, and ratios of the beneficial agents. The parameters may be varied singly or in combination, and further variations may also be incorporated, such as variations in the amounts or concentrations of beneficial agent in the various compartments.

Each of the three parameters refers to the permeable wall through which the beneficial agent diffuses. This may be the entire wall separating the compartment from the environment external to the capsule, or the permeable portion of the wall if only a portion is permeable. Each compartment nevertheless has such a wall which is permeable to the beneficial agent.

The delivery device is preferably in the form of an elongate capsule, with the discrete wall sections, and hence the compartments, arranged longitudinally along the capsule axis. The term "surface area" refers to the inner surface of the permeable wall for a particular compartment, i.e., the surface which is first contacted by the beneficial agent residing inside the compartment prior to diffusion of the agent through the capsule wall. This does not include any internal pore surface area. The term "average wall thickness" refers to the thickness of the permeable wall averaged over the entire permeable wall associated with any single compartment. If the wall thickness is uniform for a single compartment, the term denotes the thickness at any point. If the wall thickness varies, for example by increasing from one end of the compartment to the other, the term denotes the thickness averaged over the entire permeable surface of the wall of the compartment. The term "permeability" refers to the rate at which permeating species (e.g., beneficial agents) pass through the wall material, independently of the thickness or surface area as defined above. Permeability in this sense is thus measured per unit volume of the material from which the wall is constructed.

Preferred capsules are those with a cylindrical cross section, transverse to the longitudinal axis, although rectangular and other cross sections are contemplated as well. While the diameter, or other appropriate dimension for cross sections other than cylindrical, can vary among the wall sections to achieve a variation in the surface area, it is generally most convenient to use a uniform external diameter, or at least a substantially uniform external diameter, for the entire length of the capsule. The surface area is then varied by varying the length of the section along the longitudinal axis of the capsule.

Further preferred embodiments and their features, and further objects and advantages of the invention, will be apparent from the description which follows.

DETAILED DESCRIPTION OF THE INVENTION AND PREFERRED EMBODIMENTS

Figure 1:
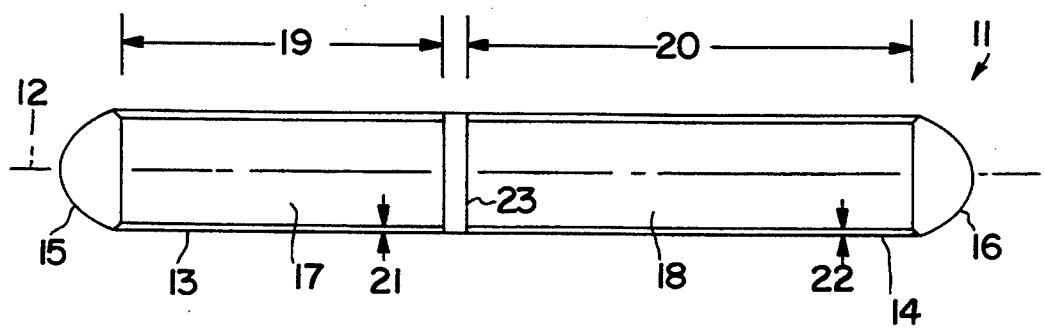
FIG. 1 is a longitudinal cross section of an elongate cylindrical capsule embodying one application of the concepts of the present invention.

The number of distinct wall segments, and hence compartments, in the device is not critical to the invention, but will simply be equal to the number of beneficial agents called for according to the therapy or regimen for which the device is designed. In most cases, the number of compartments will be from two to five, and often just two.

When any one of the three parameters listed above is varied between the wall segments of adjacent compartments, the ratio of that parameter between the wall sections is not critical to the invention and may vary widely. The choice in any given case will depend on the desired ratio of delivery rates of the agents in these compartments, as well as which of the remaining two parameters, and any additional parameters other than these three, are also varied and what cumulative effect the variations will have on the delivery rate ratio.

For systems in which the surface area is varied, the ratio of surface areas of adjacent wall sections in most applications will lie between about 1.2 and about 4.0. For an elongate capsule of uniform cross section along its entire length (i.e., the cross section transverse to the longitudinal axis of the capsule), this means that the axial lengths of adjacent compartments will differ by the same ratio. The cross section shape is most conveniently circular, but other shapes, such as oval, rectangular and other polygonal cross sections, may also be used to the same effect. As alternatives to a uniform cross section, the cross section may be varied in size (e.g., diameter) from one segment to the next to achieve the surface area variation, or both the cross section and the length may be varied.

The use of a uniform cross section simplifies the manufacture of the capsule. Varying the surface area by the use of wall segments of different lengths without varying the average wall thickness or the wall permeability among the segments simplifies the manufacture even further. A disadvantage of varying only the segment length is that the amount of formulation of beneficial agent needed to fill each compartment will vary in proportion to the variation in length. This can be compensated for by varying both the wall thickness and the segment length.

For systems in which the average wall thickness is varied, the ratio of average wall thicknesses between adjacent wall sections in most applications will lie between about 1.5 and about 4.0. Where the wall thickness for each wall section is constant within that section, variations in wall thickness will require the bonding together of separately manufactured wall segments end-to-end to produce a stepwise increase in thickness. One way to avoid this is to use a tapered wall whose thickness gradually increases over a length spanning all segments, such that the average within one segment is greater than the average within the next. Such a tapered wall can be manufactured in a single piece.

For permeabilities, an appropriate measure is the normalized permeation coefficient, expressed in $\mu g\text{-cm}/\text{cm}^2\text{-sec}$. This coefficient is the product of the diffusion coefficient of the penetrant (normally a drug in solid form) through the wall material ("D") and the concentration of the penetrant in the wall material at the saturation point ("$C_s$"). This is a parameter of the wall material, independent of the thickness or shape of the wall, although the value of this parameter is temperature sensitive. In systems contemplated by the present invention, the value of the normalized permeability coefficient will generally fall within the range of about $0.3 \times 10^{-6}$ to about $30 \times 10^{-6}/\mu g\text{-cm}/\text{cm}^2\text{sec}$, or preferably within the range of about $1.0 \times 10^{-6}$ to about $1.0 \times 10^{-5}$ $\mu g\text{-cm}/\text{cm}^2\text{-sec}$. For systems in which the permeability is varied between adjacent wall segments, the ratio of normalized permeation coefficients $D \times C_s$ between these segments will in most applications lie between about 1.1 and about 5.0.

The semi-permeable wall segments can be manufactured from any of a wide variety of materials, the range of which are well known among those skilled in the art and technology of diffusional drug delivery capsules. Polymeric materials are particularly useful, however, since they can be selected, formulated and modified to achieve the desired permeability. Homopolymers, copolymers, block copolymers and polymer blends may be used. Examples are polyethylene vinyl acetates, polyvinyl acetates, ethylene vinyl acetates, polyurethanes, polyetherurethanes, silicones, polyterephthalates, polyalkylene glycols, copoly(n-butylehtyleneacrylate), copoly(ethylenevinyl-n-butyrate, and cellulosic materials such as cellulose esters, cellulose ethers, and cellulose ester-ethers. Presently preferred materials are thermoplastic elastomers. Permeability of the wall can be varied by the appropriate selection of polymers from among these types.

Permeability may be further varied by the inclusion of modifiers in the wall composition. Modifiers may be selected either to decrease or to increase the permeability. Examples of modifiers which decrease the permeability are polyacrylate, polymethacrylate, polysulfone, polyacrylic ester, polyacrylonitrile, polyacrylamide, polystyrene, polycaprolactam, polyhexamethylene adipamide, polyhexamethylene sebacamide, polyepoxide, and polyformaldehyde. Examples of modifiers which increase the permeability are polyvinyl alcohol; poly(1,4-anhydro-β-D-mannuronic acid); polyesters derived from the condensation of a polyhydric alcohol and a polyfunctional acid whose functional groups are hydroxyl groups, carboxyl groups and the like; polysaccharides, hydroxyalkylcelluloses having molecular weights of 9,000 to 35,000; and polyalkylene glycol. Depending on its need, the modifier may be present in the wall material in an amount ranging from about 5% to about 50% by weight.

A still further means of varying the permeability is to form the wall segments of polymer blends using varying amounts of individual polymers in each blend. One example is a blend of polyvinyl acetate with polyethylene. An analogous result may be obtained with block copolymers, with variations introduced by varying the number or size of one type of block relative to the other or others. One example is a block copolymer comprised of blocks of a crystalline polymer joined to blocks of an amorphous polymer. Variations in permeability will result, for example, by varying the ratio of the number of crystalline segments to the number of amorphous segments, or by varying the average size of the crystalline segments relative to the average size of the amorphous segments. An example of such a block copolymer is one in which the crystalline segments are polybutylene terephthalate and the amorphous segments are long-chain polyether glycols. Block copolymers of this type are available from E.I. du Pont de Nemours & Co., Inc., Wilmington, Del., U.S.A., under the trade name HYTREL ®.

Aside from permeability considerations, other physical characteristics of the wall such as workability and flexibility, lowering of the second-order phase transition temperature and modification of the elastic modulus may further be enhanced by the inclusion of a plasticizer. Typical plasticizers extend to both straight-chain and branched-chain plasticizers, cyclic plasticizers, acrylic plasticizers and heterocyclic plasticizers. Examples of classes of suitable plasticizers are known to those skilled in the art. Plasticizers when included will generally comprise from about 1% to about 45% by weight of the wall composition.

The beneficial agent is preferably formulated in a composition which will promote a zero-order delivery rate. This may be achieved in a variety of ways known to those skilled in the art. As mentioned above, one particularly effective method is to combine the beneficial agent with a dilution agent in which the beneficial agent is only partially soluble, and to use a proportion of beneficial agent to dilution agent which exceeds the solubility limit. The undissolved amount of beneficial agent, which is generally solid, will then exist as particles dispersed through the dilution agent, which will contain dissolved beneficial agent at the solubility limit. Diffusion of the beneficial agent from the formulation into the semi-permeable wall of the capsule will occur primarily from the dilution agent due to the greater interfacial contact between the dilution agent and the wall. This will be accompanied by diffusion of beneficial agent through the dilution agent due to the concentration gradients caused by the outward diffusion, and by the dissolving of further beneficial agent from the dispersed particles to return the dissolved concentration to the solubility limit. Thus, the amount of beneficial agent forming the dispersed phase becomes depleted, while the concentration of beneficial agent in the continuous phase (dissolved in the dilution agent) remains approximately constant, until all of the beneficial agent has dissolved. In accordance with this mechanism, the solubility of the beneficial agent in the dilution agent is preferably less than 10% by weight, and most preferably about 1% to about 4%.

The dilution agent may be any of a variety of substances meeting the above description. The dilution agent may be a solid, semi-solid or liquid, provided that the beneficial agent dissolves to the desired extent in the dilution agent and diffuses through it in response to a concentration gradient. To maintain the integrity of the interface at the inner surface of the capsule wall, the dilution agent will be a substance which is not soluble in the wall material, and one in which the wall material is not soluble. Examples of dilution agents which can be used in the practice of this invention are silicone oils, vegetable oils, mineral oil, waxes, polymer blends such as polyethylene glycol blends, and gels of various kinds. Solids and semi-solids offer the advantage of permitting preparation of the formulation by such processes as extrusion.

Figure 2:
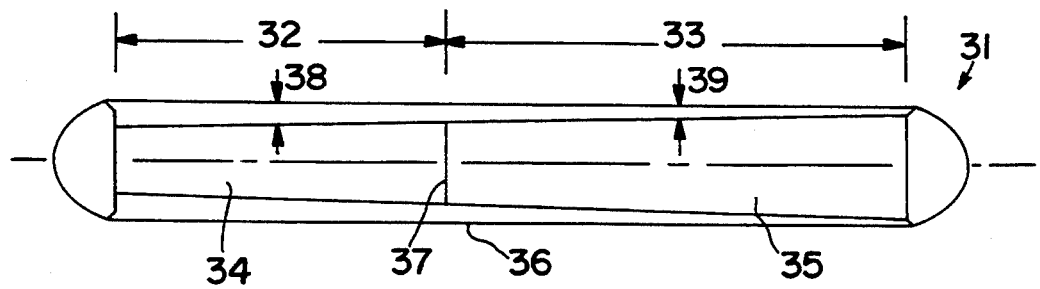
FIG. 2 is a longitudinal cross section of an elongate cylindrical capsule embodying a second application of the concepts of the present invention.

Illustrations of two delivery devices in accordance with this invention are shown in FIGS. 1 and 2, respectively.

In FIG. 1, the device 11 is a cylindrical body shown in longitudinal cross section along the longitudinal axis 12. The enclosure of the device consists of two cylindrical sections 13, 14 joined together end-to-end to form the side wall, plus two end caps 15, 16, one at each end. The two wall sections define two internal compartments 17, 18, for retaining two different beneficial agents. In this device, the difference in delivery rate between the two beneficial agents is achieved by providing the two wall sections with both different axial lengths 19, 20 and different thicknesses 21, 22. Since the two wall sections differ in thickness by a step difference, they are constructed separately and joined together at their ends, optionally through a disk 23 to which each is bonded. The disk 23 itself is impermeable to either beneficial agent, thereby eliminating any interdiffusion between the two compartments. Where the beneficial agents are lowly soluble in the dilution agents, interdiffusion is negligible and a disk 23 in not required. By "lowly soluble" as used herein and the appended claims is meant a beneficial agent with a solubility in the dilution agent that is no greater than 10 mg/gm (one percent).

In FIG. 2, a device 31 is shown with the same external dimensions and shape as the device 11 of FIG. 1. In addition, the lengths 32, 33 of the two beneficial agent compartments 34, 35 are the same as those of the corresponding compartments 24, 25 in the FIG. 1 device. The same wall segment parameters are varied as well, but the thickness variation is achieved by using a single-piece cylinder 36 with a wall thickness which increases from one end to the other at a uniform rate. The lengths 32, 33 of the two beneficial agent compartments are thus defined by the relative amounts of the two beneficial agent formulations within the device. The interface 37 between the two compartments is not a physical barrier but is instead defined by the step change in composition between the two formulations. Due to the tapering of the cylinder wall thickness, the average or mid-length thickness 38 of that portion of the wall surrounding one compartment differs from the average or mid-length thickness 39 of that portion of the wall surrounding the other compartment.

The present invention may be used for the administration of multiple beneficial agents in general, including any combination of two or more physiologically or pharmacologically active substances. Included among the types of agents which meet this description are biocides, sterilization agents, nutrients, vitamins, food supplements, sex sterilants, fertility inhibitors and fertility promoters. Drug agents include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention include, but are not limited to, prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-estradiol, ethinyl estradiol, ethinyl estradiol 3-methyl ether, pednisolone, 17-$\beta$-hydroxyprogesterone acetate, 19-nor-progesterone, norgestrel, norethindrone, norethisterone, norethiederone, progesterone, norgesterone, norethynodrel, gestodene, ST-1435, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, endlapriat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

The beneficial agent can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations can be used. Derivatives such as esters, ethers and amides can be used.

The diffusional delivery which is provided by devices in accordance with this invention may be for therapeutic purposes, nutritional purposes, preventive purposes, and a wide variety of situations in general. The environments in which the devices may be used include physiological environments within the body of a human or animal, or aqueous environments such as pools, tanks, reservoirs, moistened ground, intravenous bottles, and the like serving recreational, industrial, agricultural, medical, or residential purposes. Animals to whom drugs may be administered using systems of this invention include humans and other mammals and warm-blooded animals in general, avians, reptiles and fishes. Household animals, sport animals, farm animals, laboratory animals and zoo animals are included. The invention is of particular interest for application to humans and household, sport and farm animals, particularly mammals. For the administration of beneficial agents to animals, the devices of the present invention may be implanted subcutaneously or intraperitoneally or they may be applied vaginally. Devices of the invention may also be administered to the rumen of ruminant animals, in which embodiment the devices further comprise a density element for maintaining the device in the rumen for extended periods of time of up to 120 days or longer. Density elements are well known in the art of drug delivery devices. In a presently preferred embodiment, the device is an implant and the environment of use is a human.

The devices of the present invention can be prepared by processes known in the art, such as extrusion, molding, filling, and the like. For example, a device of two wall segments and having liquid or semisolid beneficial agent formulations can be manufactured by first injection-molding the wall segments. Two segments, of different polymers and/or having differing wall thicknesses and/or of different lengths, are cut to the desired length, and each of the segments is sealed on one end by injection-molding to form a cup at that end. The cups are filled with the appropriate beneficial agent formulation. A plug may or may not then be placed in the open end of one of the filled cups, depending on whether the two agent formulations would remain separate within the device or would become mixed together upon contact with each other. The filled cups are then joined together to seal their open ends in an injection-molding operation to form the final system with a smooth outer wall. An alternative method of manufacture is to attach the two segments together first to form a dual cup with a center divider and open at each end. Each segment is then filled with the appropriate beneficial agent formulation, and the device is then sealed at both ends in a final injection-molding operation.

For a device having a solid beneficial agent formulation, manufacture can be by coextruding the agent formulation with the polymer wall, similar to a coated wire, to provide a beneficial agent core surrounded by a polymer wall of a particular thickness and composition. Each segment is then cut to length, sealed at one end, and joined together as discussed above. Alternatively, the beneficial agent formulations can be separately extruded and then inserted into the wall segments, either before or after they are bonded together, as discussed above.

For a device having a continuous wall of varying thickness along its length, the wall can be formed by injection molding, after which the beneficial agent formulations can be added and the ends selated as discussed above.

The following examples are offered by way of illustration and not of limitation.

EXAMPLES

Calculations were performed to determine parameters for a diffusional delivery device of the configuration shown in FIG. 1, for the simultaneous delivery of 17$\beta$-estradiol (abbreviated "E2") and levonorgestrel (abbreviated "LNG") at a target E2:LNG ratio of 2.5:1 on a weight basis. Three dosage rates were used, expressed in $\mu$g/day as 25:10 (E2:LNG), 50:20 and 100:40, and calculations were performed for delivery time periods of 12 months and 24 months. The maximum delivery rates for a 24-month system are 32 $\mu$g/day LNG and 80 $\mu$g/day E2. The device was designed with end and center seals (elements 15, 16 and 23 of FIG. 1) of approximately 0.1 cm each in thickness, thereby adding a total of approximately 0.3 cm to the length of the device. The external dimensions of the device were selected to permit the device to fit inside an 11-gauge trochar. The overall length was thus limited to a maximum of 4.3 to 4.5 cm with an active delivery length limited to a maximum of 4.0 cm, and the outside diameter was limited to a maximum of 0.24 cm. Two diameters within this limit were used in the calculations. The initial amount of drug in each segment of the device was in excess by 20% of the amount needed, to maintain saturation during delivery. The results of the calculations are shown in Table I.

Similar calculations were performed using gestodene (abbreviated "GTD") in place of LNG. The range of delivery rates used was the same as that used for Table I, as was the delivery ratio of 2.5, even though GTD is somewhat more potent than LNG. The results of these calculations are shown in Table II.

For Table III, the known steroid ST-1435 (16-methylene-17$\alpha$-acetoxy -19-nor-4-pregnene-3,20-dione) was substituted for LNG and GTD. With a melting point of 175° C., lower than that of both LNG and GTD, ST-1435 has a higher permeation rate through a given polymer. This is offset, however, by the lower potency compared to both LNG and GTD. The dose was varied between 20 and 80 $\mu$g/day.

TABLE I

Calculated Design Parameters for Device Delivering Levonorgestrel (LNG) and 17$\beta$-Estradiol (E2) At Specified Rates and Rate Ratios and Over Specified Periods of Time

| Agent | Wall D × $C_s$ ($\mu$g-cm/cm²-sec) | Total Agent Dilivere d (mg) | Segment Length (cm) | Wall Thickness (mil) | Drug Content (mg) | (load) |
|---|---|---|---|---|---|---|
| I. Delivery Span: 12 months; Delivery Rates: LNG = 10 $\mu$g/day; E2 = 25 $\mu$g/day | | | | | | |
| A. Capsule Diameter 0.094" (0.24 cm) | | | | | | |
| LNG | 1 × 10⁻⁶ | 3.65 | 1.56 | 4 | 5.8 | 10 |
| E2 | 4.5 × 10⁻⁶ | 9.13 | 0.87 | 4 | 11.2 | 30 |
| B. Capsule Diameter 0.085" (0.22 cm) | | | | | | |
| LNG | 1 × 10⁻⁶ | 3.65 | 1.73 | 4 | 5.2 | 10 |
| E2 | 4.5 × 10⁻⁶ | 9.13 | 0.96 | 4 | 11.5 | 40 |
| II. Delivery Span: 24 months; Delivery Rates: LNG = 10 $\mu$g/day; E2 = 25 $\mu$g/day; Capsule Diameter 0.094" (0.24 cm) | | | | | | |
| LNG | 1 × 10⁻⁶ | 7.3 | 1.56 | 4 | 11.6 | 20 |
| E2 | 4.5 × 10⁻⁶⁶ | 18.3 | 0.87 | 4 | 22.4 | 60 |
| III. Delivery Span: 12 months; Delivery Rates: LNG = 20 $\mu$g/day; E2 = 50 $\mu$g/day | | | | | | |
| A. Capsule Diameter 0.094" (0.24 cm) | | | | | | |
| LNG | 6 × 10⁻⁶ | 7.3 | 1.05 | 8 | 9.7 | 30 |
| E2 | 4.5 × 10⁻⁶ | 18.3 | 1.74 | 4 | 22.8 | 35 |
| B. Capsule Diameter 0.085" (0.22 cm) | | | | | | |
| LNG | 6 × 10⁻⁶ | 7.3 | 1.16 | 8 | 9.8 | 35 |
| E2 | 4.5 × 10⁻⁶ | 18.3 | 1.93 | 4 | 23.2 | 40 |
| IV. Delivery Span: 24 months; Delivery Rates: LNG = 20 $\mu$g/day; E2 = 50 $\mu$g/day; Capsule Diameter 0.094" (0.24 cm) | | | | | | |
| LNG | 6 × 10⁻⁶ | 14.6 | 1.05 | 8 | 16.1 | 50 |
| E2 | 3 × 10⁻⁶ | 36.6 | 2.61 | 4 | 44 | 45 |
| V. Delivery Span: 12 months; Delivery Rates: LNG = 40 $\mu$g/day; E2 = 100 $\mu$g/day | | | | | | |
| A. Capsule Diameter 0.094" (0.24 cm) | | | | | | |
| LNG | 6 × 10⁻⁶ | 14.6 | 1.05 | 4 | 17.7 | 45 |
| E2 | 6 × 10⁻⁶ | 36.6 | 2.61 | 4 | 44 | 45 |
| B. Capsule Diameter 0.085" (0.22 cm) | | | | | | |
| LNG | 6 × 10⁻⁶ | 14.6 | 1.16 | 4 | 17.4 | 50 |
| E2 | 7 × 10⁻⁶ | 36.6 | 2.48 | 4 | 45 | 60 |
| VI. Delivery Span: 24 months; Delivery Rates LNG = 32 $\mu$g/day; E2 = 80 $\mu$g/day; Capsule Diameter 0.094" (0.24 cm) | | | | | | |
| LNG | 4.4×10⁻⁶ | 23.4 | 1.14 | 4 | 28 | 65 |
| E2 | 4.4×10⁻⁶ | 58.4 | 2.86 | 4 | 70 | 65 |

TABLE II

Calculated Design Parameters for Device Delivering Gestodene (GTD) and 17$\beta$-Estradiol (E2) At Specified Rates and Rate Ratios and Over Specified Periods of Time

| Agent | Wall D × $C_s$ ($\mu$g-cm/cm²-sec) | Total Agent Dilivere d (mg) | Segment Length (cm) | Wall Thickness (mil) | Drug Content (mg) | (load) |
|---|---|---|---|---|---|---|
| I. Delivery Span: 12 months; Delivery Rates: GTD = 10 $\mu$g/day; E2 = 25 $\mu$g/day | | | | | | |
| A. Capsule Diameter 0.094" (0.24 cm) | | | | | | |
| GTD | 2.9 × 10⁻⁶ | 3.65 | 1.08 | 8 | 6.7 | 20 |
| E2 | 4.5 9.13 × 10⁻⁶ | | 0.87 | 4 | 11.2 | 30 |
| B. Capsule Diameter 0.085" (0.22 cm) | | | | | | |

TABLE II-continued

Calculated Design Parameters for Device Delivering Gestodene (GTD) and 17β-Estradiol (E2) At Specified Rates and Rate Ratios and Over Specified Periods of Time

| Agent | Wall $D \times C_s$ (μg-cm/-cm²-sec) | Total Agent Dilivere d (mg) | Segment Length (cm) | Wall Thickness (mil) | Drug Content (mg) | (load) |
|---|---|---|---|---|---|---|
| GTD | $2.9 \times 10^{-6}$ | 3.65 | 1.2 | 8 | 5.7 | 20 |
| E2 | $4.5 \times 10^{-6}$ | 9.13 | 0.96 | 4 | 11.5 | 40 |

II. Delivery Span: 24 months; Delivery Rates: GTD = 10 μg/day; E2 = 25 μg/day; Capsule Diameter 0.094" (0.24 cm)

| GTD | $2.9 \times 10^6$ | 7.3 | 1.08 | 8 | 11.7 | 35 |
| E2 | $4.5 \times 10^{-6}$ | 18.3 | 0.87 | 4 | 22.4 | 60 |

III. Delivery Span: 12 months; Delivery Rates: GTD = 20 μg/day; E2 = 50 μg/day

A. Capsule Diameter 0.094" (0.24 cm)

| GTD | $2.9 \times 10^{-6}$ | 7.3 | 1.62 | 6 | 11 | 20 |
| E2 | $4.5 \times 10^{-6}$ | 18.3 | 1.74 | 4 | 22.8 | 35 |

B. Capsule Diameter 0.085" (0.22 cm)

| GTD | $2.9 \times 10^{-6}$ | 7.3 | 1.79 | 6 | 12.1 | 25 |
| E2 | $4.5 \times 10^{-6}$ | 18.3 | 1.93 | 4 | 23.2 | 40 |

IV. Delivery Span: 24 months; Delivery Rates: GTD = 20 μg/day; E2 = 50 μg/day; Capsule Diameter 0.094" (0.24 cm)

| GTD | $2.9 \times 10^{-6}$ | 14.6 | 1.08 | 4 | 20 | 50 |
| E2 | $3 \times 10^{-6}$ | 36.6 | 2.61 | 4 | 44 | 45 |

V. Delivery Span: 12 months; Delivery Rates: GTD = 40 μg/day; E2 = 100 μg/day

A. Capsule Diameter 0.094" (0.24 cm)

| GTD | $6 \times 10^{-6}$ | 14.6 | 1.05 | 4 | 19.7 | 50 |
| E2 | $6 \times 10^{-6}$ | 36.6 | 2.61 | 4 | 44 | 45 |

B. Capsule Diameter 0.085" (0.22 cm)

| GTD | $6 \times 10^{-6}$ | 14.6 | 1.16 | 4 | 17.4 | 50 |
| E2 | $7 \times 10^{-6}$ | 36.6 | 2.48 | 4 | 45 | 60 |

VI. Delivery Span: 24 months; Delivery Rates GTD = 32 μg/day; E2 = 80 μg/day; Capsule Diameter 0.094" (0.24 cm)

| GTD | $4.4 \times 10^{-6}$ | 23.4 | 1.14 | 4 | 28 | 65 |
| E2 | $4.4 \times 10^{-6}$ | 58.4 | 2.86 | 4 | 70 | 65 |

TABLE III

Calculated Design Parameters for Device Delivering ST1435 (ST) and 17β-Estradiol (E2) At Specified Rates and Rate Ratios and Over Specified Periods of Time

| Agent | Wall $D \times C_s$ (μg-cm/-cm²-sec) | Total Agent Dilivere d (mg) | Segment Length (cm) | Wall Thickness (mil) | Drug Content (mg) | (load) |
|---|---|---|---|---|---|---|

I. Delivery Span: 12 months; Delivery Rates: ST = 20 μg/day; E2 = 25 μg/day

A. Capsule Diameter 0.094" (0.24 cm)

| ST | $5 \times 10^{-6}$ | 7.3 | 1.25 | 8 | 9.6 | 25 |
| E2 | $4.5 \times 10^{-6}$ | 9.13 | 0.87 | 4 | 11.2 | 30 |

B. Capsule Diameter 0.085" (0.22 cm)

| ST | $5 \times 10^{-6}$ | 7.3 | 1.38 | 8 | 10 | 30 |
| E2 | $4.5 \times 10^{-6}$ | 9.13 | 0.96 | 4 | 11.5 | 40 |

II. Delivery Span: 24 months; Delivery Rates: ST = 20 μg/day; E2 = 25 μg/day; Capsule Diameter 0.094" (0.24 cm)

| ST | $5 \times 10^{-6}$ | 14.6 | 1.25 | 8 | 19.2 | 50 |
| E2 | $4.5 \times 10^{-6}$ | 18.3 | 0.87 | 4 | 22.4 | 60 |

III. Delivery Span: 12 months; Delivery Rates: ST = 40 μg/day; E2 = 50 μg/day

A. Capsule Diameter 0.094" (0.24 cm)

| ST | $5\;33 \times 10^{-6}$ | 14.6 | 1.25 | 4 | 18.7 | 40 |
| E2 | $4.5 \times 10^{-6}$ | 18.3 | 1.74 | 4 | 22.8 | 35 |

B. Capsule Diameter 0.085" (0.22 cm)

| ST | $5 \times 10^{-6}$ | 14.6 | 1.38 | 4 | 20.7 | 50 |
| E2 | $4.5 \times 10^{-6}$ | 18.3 | 1.93 | 4 | 23.2 | 40 |

IV. Delivery Span: 24 months; Delivery Rates: ST = 40 μg/day; E2 = 50 μg/day; Capsule Diameter 0.094" (0.24 cm)

| ST | $3.7 \times 10^{-6}$ | 29.2 | 1.7 | 4 | 37.8 | 60 |
| E2 | $4 \times 10^{-6}$ | 36.6 | 1.96 | 4 | 44.1 | 60 |

V. Delivery Span: 12 months; Delivery Rates: ST = 80 μg/day; E2 = 100 μg/day

A. Capsule Diameter 0.094" (0.24 cm)

| ST | $7 \times 10^{-6}$ | 29.2 | 1.78 | 4 | 36.7 | 55 |
| E2 | $7 \times 10^{-6}$ | $102\;10^{36.6}$ | 2.22 | 4 | 45.8 | 55 |

B. Capsule Diameter 0.085" (0.22 cm)

| ST | $7.8 \times 10^{-6}$ | 29.2 | 1.78 | 4 | 34.8 | 65 |
| E2 | $7.8 \times 10^{-6}$ | 36.6 | 2.22 | 4 | 43.4 | 65 |

A presently preferred system in accordance with this invention is a capsule of the configuration shown in FIG. 1 for the simultaneous delivery of ST-1435 and 17-β-estradiol (E2) at nominal rates of 40 μg/day and 50 μg/day, respectively, for twelve months. The capsule wall through which the drugs diffuse is made of either a polyetherurethane (such as PELLETHANE 2103-80A, a product of Union Carbide Corp., Danbury, Conn., U.S.A.) or a copolymer of ethylene and vinyl acetate with a vinyl acetate content of 18% (EVA 18). The wall thickness for both sections is within the range of 3 to 5 mil ($7.62 \times 10^{-3}$ to $12.7 \times 10^{-3}$ cm) with an outside diameter of 0.094 inch (0.24 cm). The length of the ST-1435 segment is 1.25 cm and the length of the E2 segment is 1.75 cm. The total system length (including end caps and intercompartment seal) is 3.3 to 3.5 cm. The core formulations consist of each drug blended in silicone oil, 100 cs grade.

The foregoing is offered primarily for purposes of illustration. It will be readily apparent to those skilled in the art that the number and arrangement of parts, materials of construction, dimensions, and other parameters of the system may be further modified or substituted in various ways without departing from the spirit and scope of the invention.

What is claimed is:

1. A diffusional delivery device for placement in an aqueous environment for delivery to said environment of a plurality of beneficial agents each at a preselected rate for a predetermined duration of use, said device comprising:
a plurality of beneficial agent formulations, each formulation being in physical contact with its adjacent formulation and each said beneficial agent formulation comprising said beneficial agent and a dilution agent in which it is lowly soluble, the amount of said beneficial agent in said formulation being in excess of saturation in their respective dilution agent throughout said duration of use,
an elongate enclosure defined by a wall at least a portion of which is permeable by diffusion to said beneficial agents, said formulation together with said segment of said wall defining a plurality of compartments along said enclosure,
each of said wall segments being capable of releasing said beneficial agent confined therein by diffusion at the preselected rate for each said beneficial agent, thereby causing preselected quantities of beneficial agent to diffuse from said plurality of compartments through said wall segments per unit time when said device is placed in said aqueous environment.

2. A diffusional delivery device in accordance with claim in which said wall is divided into two to five such wall segments, thereby defining two to five said compartments.

3. A diffusional delivery device in accordance with claim 1 in which said wall is divided into two such wall segments, thereby defining two said compartments.

4. A diffusional delivery device in accordance with claim 1 in which said plurality of wall segments include two such wall segments differing in surface area by a ratio of from about 1.2 to about 4.0.

5. A diffusional delivery device in accordance with claim 1, said device having a longitudinal axis and wherein said plurality of wall segments have cross sections transverse to said longitudinal axis which are substantially identical, with two of said wall segments differing in axial length by a ratio of from about 1.2 to about 4.0.

6. A diffusional delivery device in accordance with claim 1 said device having a longitudinal axis and wherein said plurality of wall segments have cross sections transverse to said longitudinal axis which are substantially identical, with two of said wall segments differing in average wall thickness by a ratio of from about 1.5 to about 4.0.

7. A diffusional delivery device in accordance with claim 1 said device having a longitudinal axis and wherein said plurality of wall segments have cross sections transverse to said longitudinal axis which are substantially identical, with two of said wall segments differing in both axial length and average wall thickness.

8. A diffusional delivery device in accordance with claim 1 said device having a longitudinal axis and wherein said plurality of wall segments have cross sections transverse to said longitudinal axis which are substantially identical, with two of said wall segments differing in axial length by a ratio of from about 1.2 to about 4.0, and in average wall thickness by a ratio of from about 1.5 to about 4.0.

9. A diffusional delivery device in accordance with claim 1 in which said elongate enclosure terminates in first and second ends and said enclosing wall is of continuously increasing thickness from said first end to said second end, whereby the average wall thicknesses of successive wall segments increase from said first end to said second end and further including an interface between said beneficial agent formulations, said interface defined by a step change in composition between adjacent said beneficial agent formulations.

10. A diffusional delivery device in accordance with claim 1 further comprising a plurality of beneficial agent formulations, one such formulation filling each of said compartments and each such formulation containing a beneficial agent.

11. A diffusional delivery device in accordance with claim 1 said device having a longitudinal axis and wherein said plurality of wall segments have cross sections transverse to said longitudinal axis which are substantially identical, with at least two of said wall segments differing in chemical composition and thereby in beneficial agent permeability.

12. A diffusional delivery device in accordance with claim 1 further comprising a partition separating each pair of adjacent compartments within said elongate enclosure to substantially eliminate interdiffusion between compartments.

13. A diffusional delivery device in accordance with claim 1 in which each said beneficial agent is a solid partially soluble in said dilution agent with a solubility limit of from about 1% to about 4% by weight, and each said beneficial agent formulation comprises solid particles of said beneficial agent dispersed through a saturated solution of said beneficial agent in said dilution agent.

14. A diffusional delivery device in accordance with claim 1 said device having a longitudinal axis and further comprising a plurality of beneficial agent formulations, one such formulation filling each of said compartments and each such formulation containing a beneficial agent, and in which said plurality of wall segments have cross sections transverse to said longitudinal axis which are substantially identical, with at least two of said wall segments differing in normalized permeation coefficients relative to the drugs contained in the compartments surrounded by said wall segments.

15. A diffusional delivery device in accordance with claim 14 in which said at least two wall sections are both formed of a block copolymer comprised of blocks of crystalline and amorphous homopolymer, said block copolymer differing between said at least two wall sections in the ratio of the number of crystalline homopolymer blocks to the number of amorphous homopolymer blocks to a degree resulting in a difference in beneficial agent permeability.

16. A diffusional delivery device in accordance with claim 14 in which said at least two wall sections are both formed of a block copolymer comprised of blocks of crystalline and amorphous homopolymer, said block copolymer differing between said at least two wall sections in the ratio of the average size of said amorphous homopolymer blocks to the average size of said crystalline homopolymer blocks to a degree resulting in a difference in beneficial agent permeability.

17. A diffusional delivery device in accordance with claim 1 in which said beneficial agent formulations are selected such that in each said formulation said beneficial agent has a solubility limit of from about 1% to about 4% by weight in said dilution agent.

18. A diffusional delivery device in accordance with claim 17 in which the total amount of said beneficial agent contained in each said beneficial agent formulation differs between at least two of said compartments.

* * * * *